(12) United States Patent
Locke et al.

(10) Patent No.: US 10,064,984 B2
(45) Date of Patent: Sep. 4, 2018

(54) RECHARGING NEGATIVE-PRESSURE WOUND THERAPY

(71) Applicant: KCI Licensing, Inc., San Antonio, TX (US)

(72) Inventors: Christopher Brian Locke, Bournemouth (GB); Richard Daniel John Coulthard, Verwood (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 428 days.

(21) Appl. No.: 14/105,970

(22) Filed: Dec. 13, 2013

(65) Prior Publication Data

US 2014/0188061 A1 Jul. 3, 2014

Related U.S. Application Data

(60) Provisional application No. 61/748,707, filed on Jan. 3, 2013.

(51) Int. Cl.
*A61M 1/00* (2006.01)
(52) U.S. Cl.
CPC ........ *A61M 1/0049* (2013.01); *A61M 1/0003* (2013.01); *A61M 1/007* (2014.02);
(Continued)
(58) Field of Classification Search
CPC combination set(s) only.
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

Partial International Search Report for corresponding PCT/US2013/074935, dated Apr. 16, 2014.
(Continued)

*Primary Examiner* — Tatyana Zalukaeva
*Assistant Examiner* — Guy K Townsend

(57) ABSTRACT

A system is illustratively described herein that generally comprises a vacuum chamber, an ambient pressure chamber, a valve configured for unidirectional flow from the vacuum chamber to the ambient pressure chamber during a charging stroke, and a liquid filter configured to retain liquid in the pump. In some embodiments, the liquid filter is configured to retain liquid in the vacuum chamber during the charging stroke. In other embodiments, it may be configured to retain liquid in the ambient pressure chamber during an operating stroke. In more particular embodiments, a piston may be disposed between the vacuum chamber and the ambient pressure chamber, a passage may fluidly couple the vacuum chamber and the ambient pressure chamber, and the valve can be configured to control fluid flow through the passage. Additionally, a lumen may couple the vacuum chamber to a dressing to deliver negative pressure to the dressing in some illustrative embodiments.

12 Claims, 8 Drawing Sheets

(52) U.S. Cl.
CPC ........ *A61M 1/0009* (2013.01); *A61M 1/0088* (2013.01); *A61M 1/0017* (2014.02); *A61M 1/0052* (2014.02); *A61M 2205/073* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,084,691 A * | 4/1963 | Stoner | A61M 1/0023 215/309 |
| 3,367,332 A | 2/1968 | Groves | |
| 3,376,868 A * | 4/1968 | Mondiadis | A61M 1/0011 417/472 |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,957,051 A * | 5/1976 | Topham | A61M 1/0005 604/135 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A * | 10/1989 | Austad | A61F 5/058 602/48 |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,318,548 A * | 6/1994 | Filshie | A61M 1/0003 604/319 |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,542,939 A * | 8/1996 | Onodera | A61M 1/0009 417/469 |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,708,724 B2 * | 5/2010 | Weston | A61M 1/0088 604/304 |
| 8,007,257 B2 * | 8/2011 | Heaton | A61M 1/0011 417/472 |
| 8,287,507 B2 * | 10/2012 | Heaton | A61M 1/0011 604/313 |
| 8,535,283 B2 * | 9/2013 | Heaton | A61M 1/0011 604/319 |
| 8,679,079 B2 * | 3/2014 | Heaton | A61M 1/0011 604/313 |
| 8,728,045 B2 * | 5/2014 | Hu | A61M 1/0037 604/305 |
| 8,864,748 B2 * | 10/2014 | Coulthard | A61M 1/0088 602/42 |
| 8,986,267 B2 * | 3/2015 | Heaton | A61M 1/0011 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0198504 A1 * | 12/2002 | Risk, Jr. | A61M 1/0058 604/318 |
| 2004/0064132 A1 * | 4/2004 | Boehringer | A61M 1/0011 604/543 |
| 2004/0243105 A1 * | 12/2004 | Swan | A61M 1/0013 604/543 |
| 2006/0079852 A1 | 4/2006 | Bubb et al. | |
| 2006/0216171 A1 * | 9/2006 | Hernandez | A61M 1/0066 417/437 |
| 2008/0108977 A1 * | 5/2008 | Heaton | A61M 1/0011 604/543 |
| 2008/0200905 A1 * | 8/2008 | Heaton | A61M 1/0011 604/543 |
| 2009/0240218 A1 | 9/2009 | Braga et al. | |
| 2009/0254066 A1 * | 10/2009 | Heaton | A61M 1/0011 604/543 |
| 2009/0275922 A1 * | 11/2009 | Coulthard | A61M 1/0088 604/543 |

(56) References Cited

U.S. PATENT DOCUMENTS

| | | | |
|---|---|---|---|
| 2010/0228205 A1* | 9/2010 | Hu | A61M 1/0037 604/319 |
| 2010/0262094 A1* | 10/2010 | Walton | A61M 1/0023 604/319 |
| 2014/0188061 A1* | 7/2014 | Locke | A61M 1/0049 604/321 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| FR | 2706774 A1 | 12/1994 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 9635401 A1 | 11/1996 |
| WO | 97/18007 | 5/1997 |
| WO | 99/13793 | 3/1999 |
| WO | 2008/100438 A1 | 8/2008 |
| WO | 2009/135171 A2 | 11/2009 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.

(56) References Cited

OTHER PUBLICATIONS

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Japanese Notice of Rejection corresponding to Application No. 2015551687, dated Nov. 7, 2017.

\* cited by examiner

RECHARGING NEGATIVE-PRESSURE WOUND THERAPY

The present invention claims the benefit, under 35 U.S.C. § 119(e), of the filing of U.S. Provisional Patent Application Ser. No. 61/748,707, entitled "RECHARGING NEGATIVE-PRESSURE WOUND THERAPY," filed Jan. 3, 2013, by Locke et al., which is incorporated herein by reference for all purposes.

TECHNICAL FIELD

The present invention relates generally to tissue treatment systems and more particularly, but without limitation, to rechargeable negative-pressure wound therapy apparatuses, systems, and methods.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "negative-pressure therapy," but is also known by other names, including "negative-pressure wound therapy," "reduced-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a tissue site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

In one example embodiment, a system is described herein that generally comprises a vacuum chamber, an ambient pressure chamber, a valve configured for unidirectional flow from the vacuum chamber to the ambient pressure chamber during a charging stroke, and a liquid filter configured to retain liquid in the pump. In more particular embodiments, the liquid filter is configured to retain liquid in the vacuum chamber during the charging stroke. In other embodiments, the liquid filter is configured to retain liquid in the ambient pressure chamber during an operating stroke. In yet more particular embodiments, the pump may additionally include a piston disposed between the vacuum chamber and the ambient pressure chamber, and a passage fluidly coupling the vacuum chamber and the ambient pressure chamber, and the valve is configured to control fluid flow through the passage. Additionally, a lumen may couple the vacuum chamber to a dressing to deliver negative pressure to the dressing in some illustrative embodiments.

In other illustrative embodiments, the pump may comprise a piston chamber, a port, and a piston disposed within the piston chamber and adapted to draw fluid into the piston chamber through the port as the piston moves away from the port. A valve may be operatively coupled to the port and configured to block the fluid from exiting the piston chamber through the port as the piston moves toward the port, and a filter can be configured to separate gas from liquid in the fluid as the piston moves toward the filter, while retaining the liquid in the piston chamber.

A pump with a container is also described herein, wherein the container may be disposed within a first chamber of the pump in some illustrative embodiments. The container can be fluidly coupled to a port in the pump. A second chamber of the pump can be fluidly coupled to an external environment, such as the local ambient environment. A passage can fluidly couple the first chamber and the second chamber, and a valve can be configured for unidirectional fluid flow from the first chamber to the second chamber through the passage during a charging stroke. The filter can be configured to retain the fluid in the container during the charging stroke.

In yet other illustrative embodiments, an apparatus for applying negative-pressure therapy may include a first chamber, a port fluidly coupled to the first chamber and adapted to draw fluid into the first chamber during an operating stroke, a first valve operatively coupled to the port and configured to block fluid flow from the first chamber through the port during a charging stroke, and a second chamber fluidly coupled to an ambient pressure source. A piston may separate the first chamber and the second chamber, and a second valve can be configured for unidirectional fluid flow from the first chamber to the second chamber during the charging stroke. A filter can be configured to separate gas from liquid in the fluid as the piston moves toward the filter.

Methods for managing fluids during negative-pressure therapy are also described herein. Illustrative embodiments of the methods include coupling a pump to a porous dressing, releasing stored energy in the pump to generate negative pressure in a vacuum chamber of the pump during an operating stroke, and distributing the negative pressure to the dressing. Liquids and gases can be received into the vacuum chamber during the operating stroke. The pump can be charged to store energy while retaining the liquids within the pump during a charging stroke.

Other objects, features, and advantages of the embodiments described herein will become apparent with reference to the drawings and detailed description that follow.

DESCRIPTION OF EXAMPLE EMBODIMENTS

New and useful apparatuses, systems, and methods for applying negative-pressure therapy are set forth in the appended claims. Objectives, advantages, and a preferred mode of making and using the apparatuses, systems, and methods may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments not specifically described in detail. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
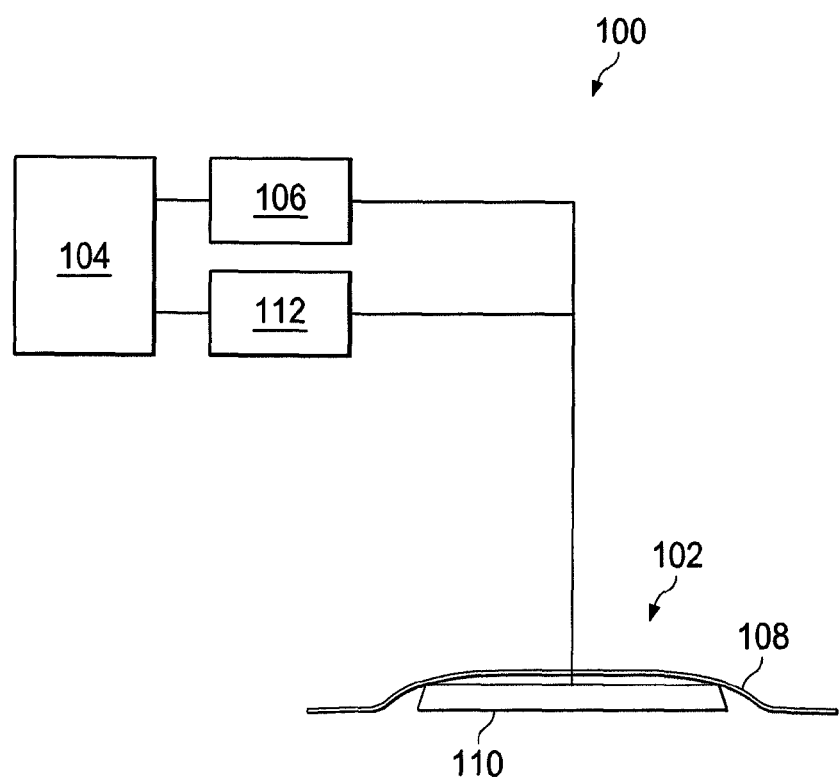
FIG. 1 is a functional block diagram of an example embodiment of a negative-pressure therapy system that can manage fluids in accordance with this specification.

FIG. 1 is a simplified functional block diagram of an example embodiment of a negative-pressure therapy system 100 that can be recharged in accordance with this specification. As illustrated, negative-pressure therapy system 100 may include a dressing 102 fluidly coupled to a negative-pressure source 104. A regulator or controller, such as regulator 106, may also be fluidly coupled to dressing 102 and negative-pressure source 104. Dressing 102 generally includes a drape, such as drape 108, and a manifold, such as pressure distribution manifold 110. Negative-pressure therapy system 100 may also include a fluid container, such as container 112, coupled to dressing 102 and negative-pressure source 104.

In general, components of negative-pressure therapy system 100 may be coupled directly or indirectly. For example, negative-pressure source 104 may be directly coupled to regulator 106 and indirectly coupled to dressing 102 through regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, pneumatic, thermal, electrical, or chemical coupling (such as a chemical bond) in some contexts.

In operation, pressure distribution manifold 110 may be placed within, over, on, or otherwise adjacent to a tissue site. Drape 108 may be placed over pressure distribution manifold 110 and sealed to tissue near the tissue site. The tissue proximate to the tissue site is often undamaged epidermis peripheral to the tissue site. Thus, dressing 102 can provide a sealed therapeutic environment proximate to a tissue site, substantially isolated from the external, ambient environment, and negative-pressure source 104 can reduce the pressure in the sealed therapeutic environment. Negative-pressure applied across a tissue site through pressure distribution manifold 110 in the sealed therapeutic environment can induce macrostrain and microstrain in the tissue site, as well as remove exudates and other fluids from the tissue site, which can be collected in container 112 and disposed of properly.

"Negative pressure" generally refers to a pressure less than a local ambient pressure, such as the ambient pressure in a local environment external to a sealed therapeutic environment provided by dressing 102. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path, a phenomenon often referred to as "suction" or "vacuum." Thus, the term "downstream" typically implies something in a fluid path relatively closer to a negative-pressure source, and conversely, the term "upstream" implies something relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative-pressure therapy may be used in certain tissue areas to grow additional tissue that may be harvested and transplanted to another tissue location.

A negative-pressure source, such as negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy.

Pressure distribution manifold 110 can be generally adapted to contact a tissue site. Pressure distribution manifold 110 may be partially or fully in contact with the tissue site. If the tissue site is a wound, for example, pressure distribution manifold 110 may partially or completely fill the wound, or may be placed over the wound. Pressure distribution manifold 110 may take many forms, and may have many sizes, shapes, or thicknesses depending on a variety of factors, such as the type of treatment being implemented or the nature and size of a tissue site. For example, the size and shape of pressure distribution manifold 110 may be adapted to the contours of deep and irregular shaped tissue sites.

More generally, a manifold is a substance or structure adapted to collect fluids from across a tissue site under negative pressure. In some embodiments, though, a manifold may also facilitate delivering fluids across a tissue site, if the fluid path is reversed or a secondary fluid path is provided, for example. A manifold may include flow channels or pathways that distribute fluids provided to and removed from a tissue site around the manifold. In some illustrative embodiments, the flow channels or pathways may be interconnected to increase uniformity of the removal or distribution of fluids across a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In some illustrative embodiments, pressure distribution manifold 110 may be a porous foam material having interconnected cells or pores adapted to apply negative pressure across a tissue site. The foam material may be either hydrophobic or hydrophilic. In one non-limiting example, pressure distribution manifold 110 can be an open-cell, reticulated polyurethane foam such as GranuFoam® dressing available from Kinetic Concepts, Inc. of San Antonio, Tex.

In an example in which pressure distribution manifold 110 may be made from a hydrophilic material, pressure distribution manifold 110 may also wick fluid away from a tissue site, while continuing to apply negative pressure to the tissue site. The wicking properties of pressure distribution manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

Pressure distribution manifold 110 may further promote granulation at a tissue site when pressure within the sealed therapeutic environment is reduced. For example, any or all of the surfaces of pressure distribution manifold 110 may have an uneven, coarse, or jagged profile that can induce microstrains and stresses at a tissue site if negative pressure is applied through pressure distribution manifold 110.

In one embodiment, pressure distribution manifold 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. Pressure distribution manifold 110 may further serve as a scaffold for new cell-growth, or a scaffold material may be used in conjunction with pressure distribution manifold 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Drape 108 is an example of a sealing member. A sealing member may be constructed from a material that can provide a fluid seal between two components or two environments, such as between a therapeutic environment and a local ambient environment. The sealing member may be, for example, an impermeable or semi-permeable, elastomeric material that can provide a seal adequate to maintain a pressure at a tissue site for a given negative-pressure source. For semi-permeable materials, the permeability generally should be low enough that a desired pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

Container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In general, negative-pressure therapy can be beneficial for conditions of all severity, but the cost and complexity of negative-pressure therapy systems often limit the application of negative-pressure therapy to large, highly-exudating wounds on patients undergoing acute or chronic care, as well as other severe conditions that are not readily susceptible to healing without application of negative pressure. For example, the complexity of many negative-pressure therapy systems can limit the ability of a person with little or no specialized knowledge from administering negative-pressure therapy. The size of many negative-pressure therapy systems may also impair mobility. Many negative-pressure therapy systems also require careful cleaning after each treatment, and may require electrical components or other powered devices to supply the negative pressure for treatment.

Eliminating power requirements can increase mobility, and generally reduce cost, as well. For example, a manually-actuated pump can be used as a source of negative pressure instead of an electrically-powered pump. In general terms, the generation of negative pressure with a manually-actuated pump is a function of receiving energy from an operator, storing the energy, and consuming the energy to perform mechanical work on a fluid. The process of receiving and storing the energy is often referred to as "charging." The energy can be stored, for example, by a combination of mechanical and pneumatic methods. For example, an operator may apply force to a crank or plunger to compress or expand an elastic element, such as a spring.

The amount of energy that can be stored in an elastic element is generally described by Hooke's law of elasticity, which is an approximation that states that the extension of an elastic element is directly proportional to the load applied to the element. Thus, for example, the amount of energy stored in a spring may be determined by the force required to deflect the spring a distance from equilibrium.

The amount of deflection a spring may undergo in a given system, though, is often constrained by the physical size of a structure within which the spring is contained. In such a constrained system, the spring rate of a spring can be increased to increase the energy storage capacity of the spring. However, increasing the spring rate also increases the force required to compress or extend the spring, and an operator may have difficulty deflecting the spring without a mechanical advantage. Means for providing a mechanical advantage include levers, screw threads, and ratchets, for example. With a mechanical advantage, an operator expends the same amount of energy to recharge the spring, but a lesser force is required. Since the energy is the same but the force is reduced, the distance over which the force is applied may be increased, or the force may be applied repeatedly.

However, leaks in a dressing can gradually erode energy stored in an elastic element of a pump. Large leaks are also common when a dressing is first applied. A manually-actuated negative-pressure therapy system can be particularly sensitive to leaks because the capacity of such a system to generate negative pressure is typically more limited than electrically-powered pumps. If a spring is used to store energy, for example, an operator may be required to periodically compress or extend the spring as the stored energy is depleted. Thus, a manually-actuated pump in a negative-pressure therapy system may require periodic charging to maintain a therapeutic pressure.

Eliminating or reducing storage capacity for exudates can also increase mobility. For example, wound fluid can be stored in an absorbent reservoir of a dressing instead of a large canister, or wound fluid can be drawn into a remote container within a pump housing. However, storing wound fluid in a dressing can increase the cost and complexity of the dressing, while drawing wound fluid into a remote container requires additional energy and can increase the cost and complexity of the pump housing.

As disclosed herein, negative-pressure therapy system 100 can overcome these challenges and others by storing and managing fluids within a piston chamber of a manually-actuated pump. Negative-pressure therapy system 100 may be particularly advantageous for application to less severe conditions where the flow of air leaking into the system exceeds the flow of other fluids from the tissue site. For example, if a dressing seal can limit leaks to less than 10 ml/h and a wound produces 60 cc of fluid over 3 days, then the air leaking into the system will greatly exceed the flow of fluids from the tissue site.

Some embodiments of negative-pressure therapy system 100 may include a pump having a piston coupled to an elastic element and disposed within a piston chamber. A charging force may be applied to compress or extend the elastic element, which moves the piston toward a port in the piston chamber. Once the charging force is removed, the spring force of the elastic element can move the piston away from the port to generate a negative pressure through the port. The negative pressure may draw fluid into the piston chamber through the port as the elastic element moves the piston away from the port. For example, if the pump is fluidly coupled to dressing 102, the pump may draw in exudates from a tissue site through dressing 102, as well as air from leaks in dressing 102. If the energy stored in the elastic element is depleted or the piston has otherwise reached a limit, the elastic element may be re-charged to maintain a therapeutic pressure. For example, a charging force may again be applied to compress or extend the elastic element, which again moves the piston toward the port. A valve may be adapted to block the fluid from exiting the piston chamber through the port as the piston moves toward the port. A filter can be configured to separate gas from liquid in the fluid as the piston moves toward the filter, while retaining the liquid in the piston chamber. For example, air from leaks may be expelled through the filter while exudates may be retained in the piston chamber.

In some illustrative embodiments, for example, a flexible pouch with at least one liquid-blocking filter may be disposed within a chamber between a piston and a port in the chamber. Negative pressure can be generated in the chamber as the piston moves away from the port, and the negative pressure can be delivered to a tissue site through the filter, pouch, and port. A one-way valve allows fluid to flow into the pouch from the tissue site as the piston moves away from the port. Another one-way valve in the piston allows fluid to flow out of the chamber as the piston advances toward the port. To recharge the pump, the piston can be moved toward the pouch and the port. As the piston contacts and compresses the pouch, air and other gases can be expelled from the pouch through the filter, but the liquid-blocking filter retains exudates and other liquids from the tissue site in the pouch. The piston can continue to advance toward the port until gases are substantially expelled from the pouch and the chamber.

In other illustrative embodiments, fluid may be drawn from a tissue site into a chamber between a piston and a port in a pump. A one-way valve allows fluid to flow into the pouch from the tissue site as the piston moves away from the port. Another one-way valve in the piston allows fluid to flow out of the chamber as the piston advances toward the port. To recharge the pump, fluids can be expelled from the chamber through the valve in the piston to a second chamber. The second chamber may include a vent with a liquid-blocking filter opposite the piston. As the piston moves away from the port to compensate for leaks, the piston moves toward the vent and expels air and other gases through the vent while the liquid-blocking filter retains exudates and other liquids within the second chamber.

In yet other illustrative embodiments, fluid may be draw from a tissue site into a chamber between a piston and a first port, and then expelled through a second port to an external container or drain. For example, the second port may be connected to a canister or bag that has the capacity to contain fluid from several charges for later disposal, or the second port may be connected to a plumbed drain.

FIGS. 2A-2D are schematic diagrams of a pump 200 in various operational states, illustrating additional details that may be associated with example embodiments of negative-pressure source 104. In this illustrative embodiment, pump 200 may include a piston chamber 202, a piston 204, an elastic element 206, an intake port 208, and an exhaust port 210. Piston chamber 202 is a substantially enclosed space, such as may be generally defined by a cylinder having a side wall 212, a base 214, and a head 216, wherein base 214 and head 216 are generally coupled to side wall 212 at opposing ends of side wall 212. Piston chamber 202 in this example embodiment is fluidly isolated from the ambient environment, except through intake port 208 and exhaust port 210, which are illustrated disposed within or fluidly coupled to base 214 and head 216, respectively.

In general, elastic element 206 may be a spring or other means for storing mechanical energy. For example, in some embodiments, elastic element 206 may be a tension spring, a compression spring, a torsion spring, a constant force spring, or a variable force spring. Elastic element 206 may be operatively engaged to piston 204 to bias piston 204 away from intake port 208. In FIGS. 2A-2D, elastic element 206 generally represents a coil tension spring coupled or otherwise operatively engaged on one end to an interior portion of piston chamber 202 and on an opposing end to piston 204.

Piston 204 can reciprocate within piston chamber 202, and generally divides piston chamber 202 into a first chamber and a second chamber, such as vacuum chamber 218 and ambient pressure chamber 220. A seal 221 may also be disposed between piston 204 and side wall 212, such as in a groove on a side wall of piston 204, to prevent fluid flow between vacuum chamber 218 and ambient pressure chamber 220 along side wall 212. Intake port 208 may fluidly couple vacuum chamber 218 to a dressing, such as dressing 102. Exhaust port 210 can fluidly couple ambient pressure chamber 220 to the ambient environment. Exhaust port 210 is preferably configured to allow gas to be expelled from ambient pressure chamber 220 as piston 204 moves toward exhaust port 210 during an operating stroke.

As illustrated in FIGS. 2A-2D, piston 204 may be a substantially rigid barrier that can reciprocate within piston chamber 202. Piston 204 may be a cylinder or disk disposed within piston chamber 202, for example. Other embodiments may include alternative types of barriers, however, such as a flexible barrier that flexes within piston chamber 202, for example.

In the example embodiment of FIGS. 2A-2D, piston 204 is substantially solid with the exception of a conduit, passage, or port, such as passage 222, which fluidly couples vacuum chamber 218 and ambient pressure chamber 220 through piston 204. Thus, ambient pressure chamber 220 is fluidly isolated from vacuum chamber 218 except through passage 222 in this illustrative embodiment. A valve 224 may be operatively coupled to piston 204 to control fluid flow between vacuum chamber 218 and ambient pressure chamber 220 through passage 222. For example, valve 224 may be a check valve or other unidirectional valve in piston 204 that allows fluid to flow from vacuum chamber 218 to ambient pressure chamber 220, but blocks flow from ambient pressure chamber 220 to vacuum chamber 218. In other embodiments, passage 222 may be a gap between piston 204 and side wall 212, and valve 224 may be a flexible seal disposed around piston 204 configured to allow fluid to flow from vacuum chamber 218 to ambient pressure chamber 220 through the gap, in which case seal 221 may be eliminated.

Pump 200 may also include a container 226 disposed within vacuum chamber 218. Container 226 is an example embodiment of container 112, which in the illustrative embodiment of FIGS. 2A-2D is a flexible, liquid-impermeable pouch adapted to expand and contract. Container 226 may be a bellows or accordion style container in some embodiments. In general, container 226 may also include a port or aperture, such as aperture 227, which may be fluidly coupled to intake port 208. At least one liquid barrier may be disposed between an interior of container 226 and the valve 224, such as within or proximate to a second aperture in container 226. As illustrated in FIGS. 2A-2D, the liquid barrier may be a filter 228 disposed in an aperture of container 226 opposite aperture 227 and facing piston 204.

Filter 228 is preferably a gas-permeable, liquid-blocking filter. In yet more particular embodiments, filter 228 may be a sintered polymer filter that swells on contact with water. Suitable polymers include, for example, fluoropolymers such as polytetrafluoroethylene (PTFE), polyvinylidene fluoride (PVdF), or fluorinated ethylenepropylene (FEP); chlorofluoropolymers, such as polychlorotrifluoroethylene (PCTFE); polyolefins such as high density polyethylene (HDPE), polypropylene (PP), cyclic olefin copolymer (COC), or polymethylpent-1-ene (PMP); polyvinyl acetate (PVAc) or ethylene vinyl acetate (EVA); polycarbonate (PC); polyesters such as polyethylene terephthalate (PET) or PET copolymers (PETG); or polysulphones or polyethersulphones. The polymer may also contain charcoal to reduce odor. Additionally, filter 228 may be coated to enhance hydrophobicity in some embodiments. Polymers may be formed into membranes or sintered (particularly for PVAc, EVA, polyolefin's, and fluoropolymers).

In more particular embodiments, a valve 230 may be coupled to intake port 208 to control fluid flow through intake port 208. For example, valve 230 may be a check valve or other unidirectional valve that allows fluid to flow through intake port 208 into container 226, but can block fluid in container 226 from flowing out through intake port 208.

In operation, pump 200 may be charged by applying a charging force to move piston 204 toward intake port 208, which extends elastic element 206 and stores mechanical energy therein. An operator may supply a charging force by applying hand pressure to a handle (not shown) coupled to piston 204, or cranking a lever-based ratchet mechanism (not shown), for example. During a charging stroke, the charging force moves piston 204 toward intake port 208, decreasing the volume of vacuum chamber 218. Since valve 230 may be configured to block fluid from flowing out through intake port 208, decreasing the volume of vacuum chamber 218 may also increase the pressure in vacuum chamber 218. The increased pressure in vacuum chamber 218 may open valve 224 to allow fluid to flow from vacuum chamber 218 to ambient pressure chamber 220 during the charging stroke.

Figure 2A:
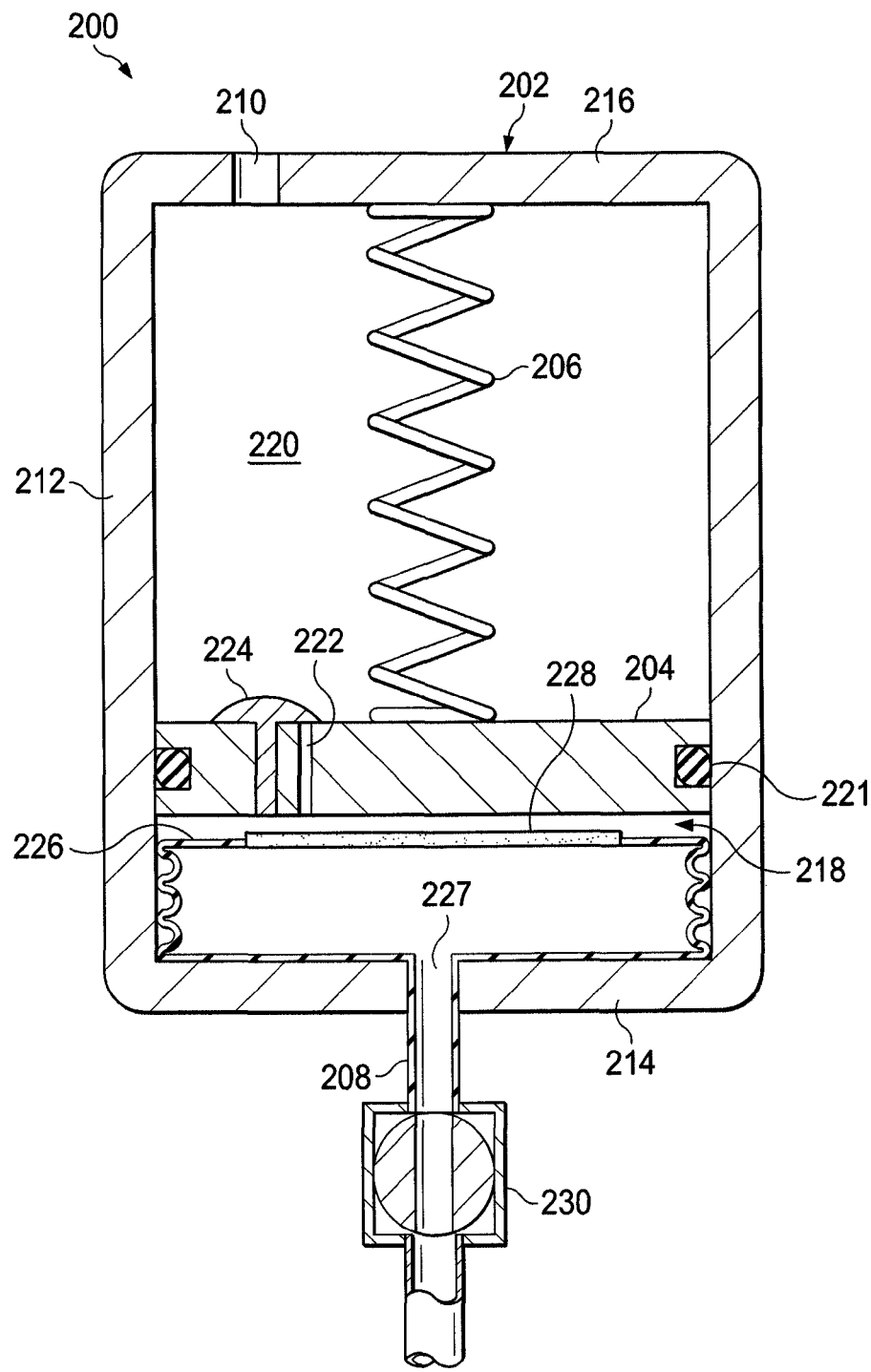
FIGS. 2A-2D are schematic diagrams illustrating additional details that may be associated with an example embodiment of a negative-pressure source in the negative-pressure therapy system of FIG. 1.

FIG. 2A, for example, illustrates a state of pump 200 in which piston 204 is at or near the limit of a charging stroke. The limit of a charging stroke may be determined by several criteria, such as a detent in piston chamber 202, the ability of an operator to overcome the force of elastic element 206, the incompressibility of container 226, or the incompressibility of fluid in container 226, for example.

Figure 2B:
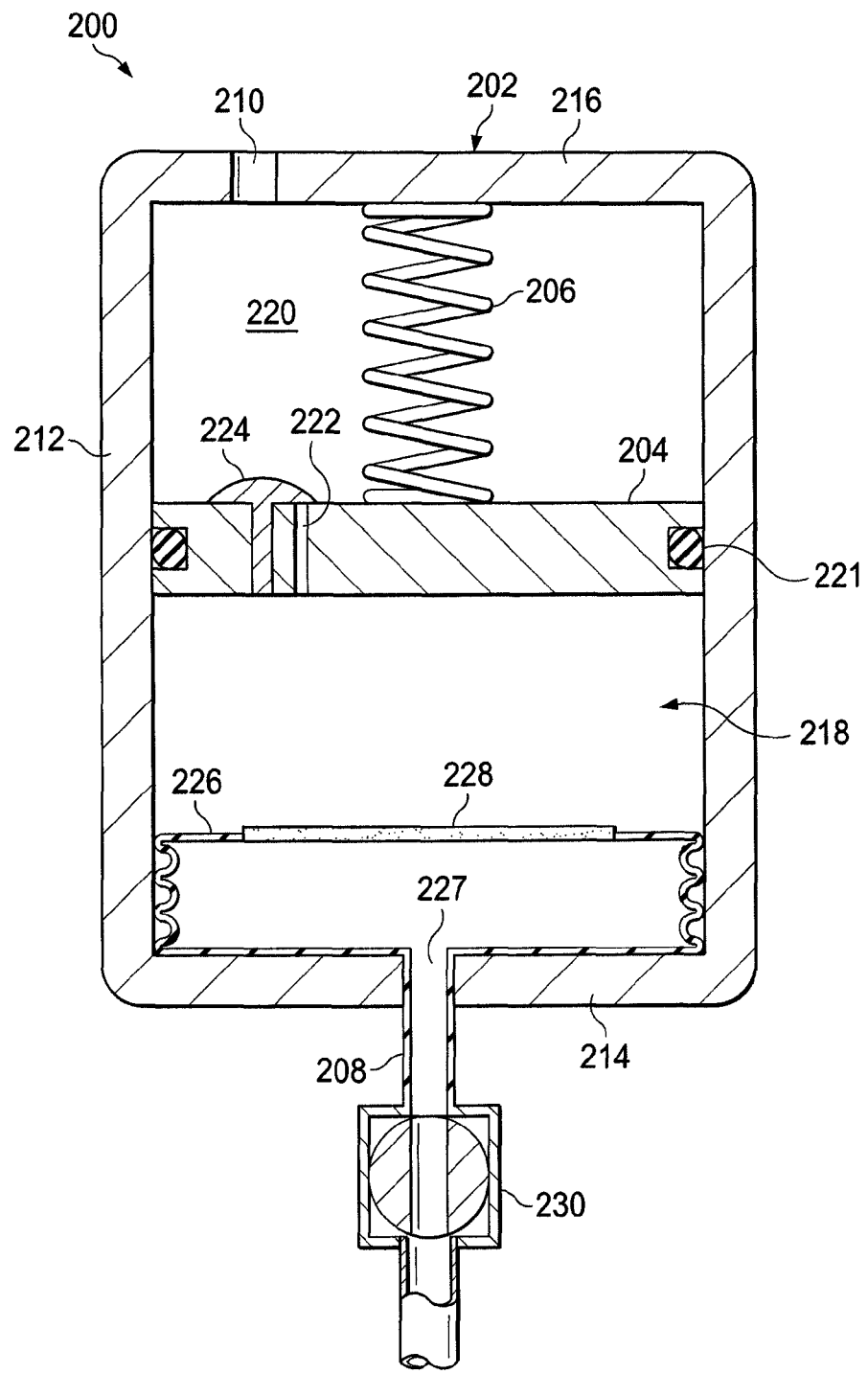

If the charging force is removed, piston 204 may move away from inlet port 208, increasing the volume of vacuum chamber 218. The movement of piston 204 away from inlet port 208 may be referred to herein as an "operating stroke." FIG. 2B illustrates a state of pump 200 in which piston 204 may be at or near a limit of an operating stroke, for example. Valve 224 may be configured to block fluid flow through passage 222 during an operating stroke. Thus, during an operating stroke, vacuum chamber 218 may become part of a closed system in which gas within vacuum chamber 218 generally behaves according to Boyle's law. In general terms, Boyle's law states that the absolute pressure and volume of a given mass of confined gas are inversely proportional, if the temperature remains unchanged within a closed system. Consequently, in expected operating conditions, the pressure within vacuum chamber 218 decreases as the volume of vacuum chamber 218 increases during an operating stroke. Filter 228 is preferably gas-permeable, and thus pressure in vacuum chamber 218 and container 226 may equalize through filter 228, resulting in a reduced pressure within container 226.

The decreasing pressure in vacuum chamber 218 resulting from the expansion of vacuum chamber 218 during an operating stroke causes a pressure differential across piston 204. To simplify further description, the force on piston 204 resulting from the pressure differential on opposing sides of piston 204 may be referred to as a "differential force." Elastic element 206 also generally exerts an elastic force on piston 204. In expected operating ranges, the force of elastic element 206 is proportional to the spring constant of elastic element 206 and to a displacement from a state of equilibrium of the ends of elastic element 206. Thus, if pressure in vacuum chamber 218 is less than pressure in ambient pressure chamber 220, the differential force on piston 204 tends to extend elastic element 206 and, consequently, the force of elastic element 206 opposes the differential force. The differential force and the force of elastic element 206 can be combined to determine a net force acting on piston 204. The net force can cause piston 204 to move reciprocally within piston chamber 202, such as along an axis parallel to side wall 212.

Elastic element 206 may be selected, adjusted, modified, tuned, or otherwise calibrated so that the net force can move piston 204 to increase the volume of vacuum chamber 218 if the pressure increases above a threshold value. In many applications, this threshold value may generally correlate to a target pressure prescribed for negative-pressure therapy, and may be referred to herein as the "therapy pressure" or "therapeutic pressure." While the amount and nature of pressure applied to a tissue site may vary according to therapeutic requirements, therapy pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

Figure 2C:
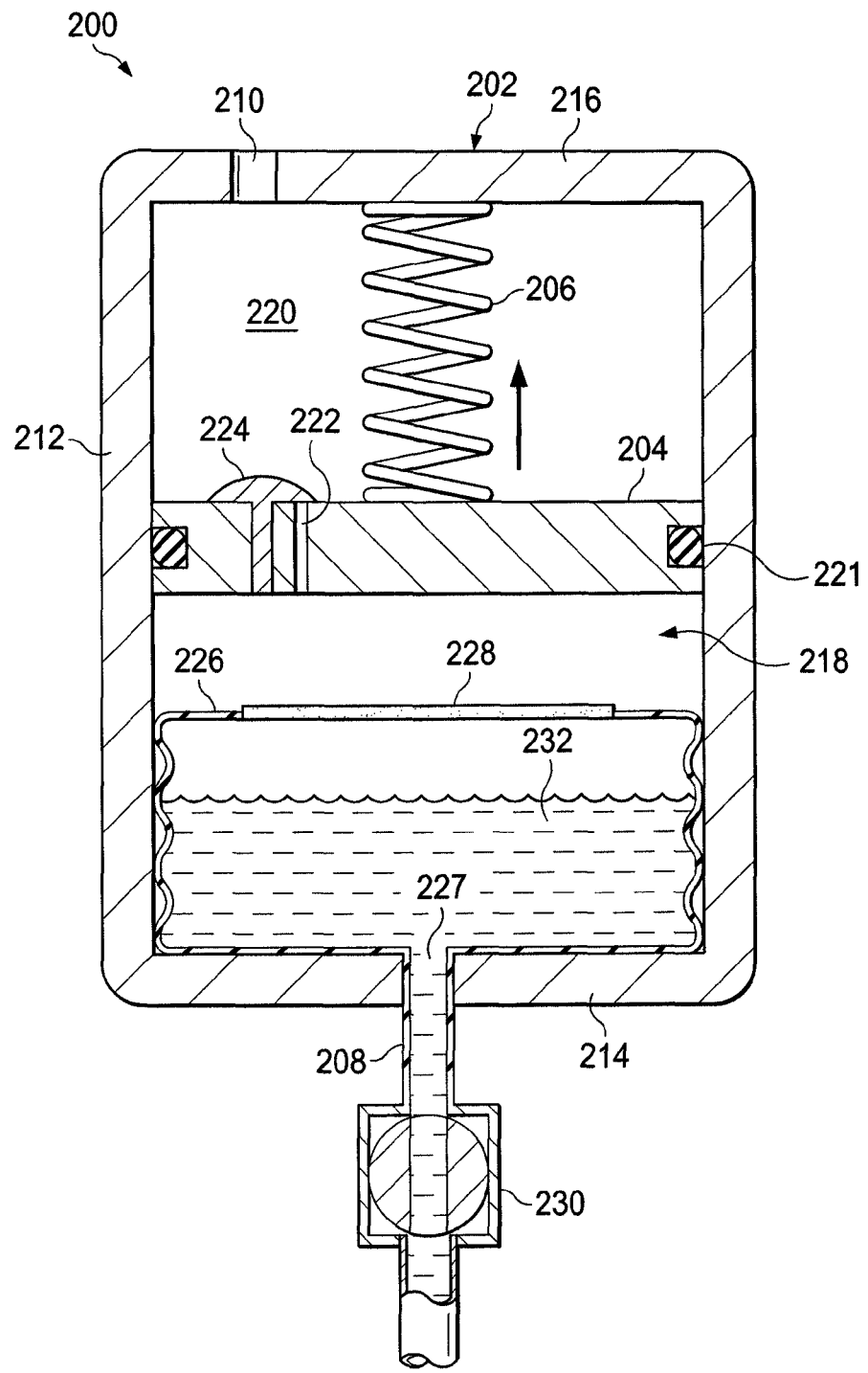
Figure 2D:
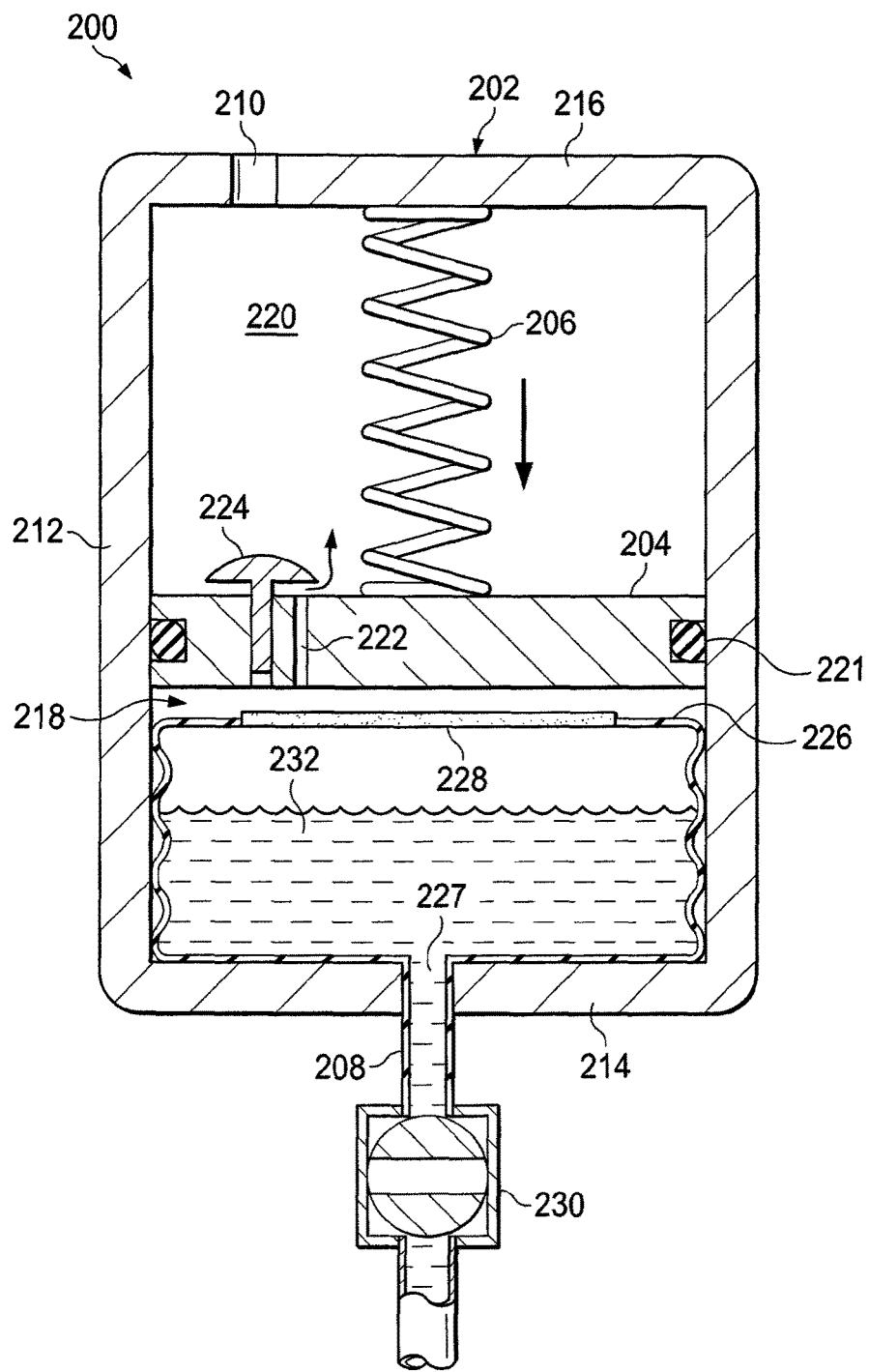

To apply negative pressure therapy to a tissue site, vacuum chamber 218 and container 226 can be fluidly coupled to a remote chamber, environment, or other location, such as a sealed therapeutic environment associated with negative-pressure therapy system 100. For example, a tube (not shown) may be coupled on a first end to inlet port 208 and on a second end to a dressing, such as dressing 102. During an operating stroke, the reduced pressure in vacuum chamber 218 may cause fluid from a tissue site to be drawn through the dressing into pump 200. FIG. 2C, for example, illustrates a state of pump 200 in which exudate 232 has been drawn into container 226 within vacuum chamber 218. Air from leaks, as well as other fluids, may also be drawn into container 226, and container 226 is adapted to expand as exudate, air, and other fluids flow into container 226.

If air from the ambient environment leaks into the system, the pressure in vacuum chamber 218 generally increases. A pressure increase in vacuum chamber 218 causes the differential force on piston 203 to decrease, and the change in net force may move piston 204 away from port 208 to increase the volume of vacuum chamber 218. The increased volume of vacuum chamber 218 reduces the pressure in vacuum chamber 218 to compensate for pressure increase caused by air leaking into vacuum chamber 218 from the ambient environment. Thus, a therapeutic pressure may be maintained at a substantially stable level until piston 204 reaches a limit of the operating stroke. The limit of the operating stroke may be determined by several criteria. For example, a detent in piston chamber 202 may limit movement of piston 204 away from port 208, or elastic element 206 may return to a state of equilibrium.

Pump 200 may be re-charged at any time during an operating stroke to maintain or extend therapeutic pressure. For example, pump 200 may be re-charged at the end of an operating stroke to maintain therapeutic pressure. To charge pump 200 again, a charging force may be applied to piston 204 again, which moves piston 204 toward intake port 208 and extends elastic element 206 again. Valve 224 can be configured to allow air and other gases to be exhausted to ambient pressure chamber 220 as piston 204 moves toward intake port 208, while valve 230 can be configured to prevent fluids from being refluxed to a tissue site through intake port 208. Moreover, if piston 204 compresses container 226, air and other gases may be expelled through filter 228, but liquids are blocked by filter 228 and retained within container 226. Thus, piston 204 may continue to move toward intake port 208 and compress container 226 until substantially all gases have been expelled from container 226, as illustrated in FIG. 4D, and gases are effectively separated from liquids during a charging stroke.

Figure 3A:
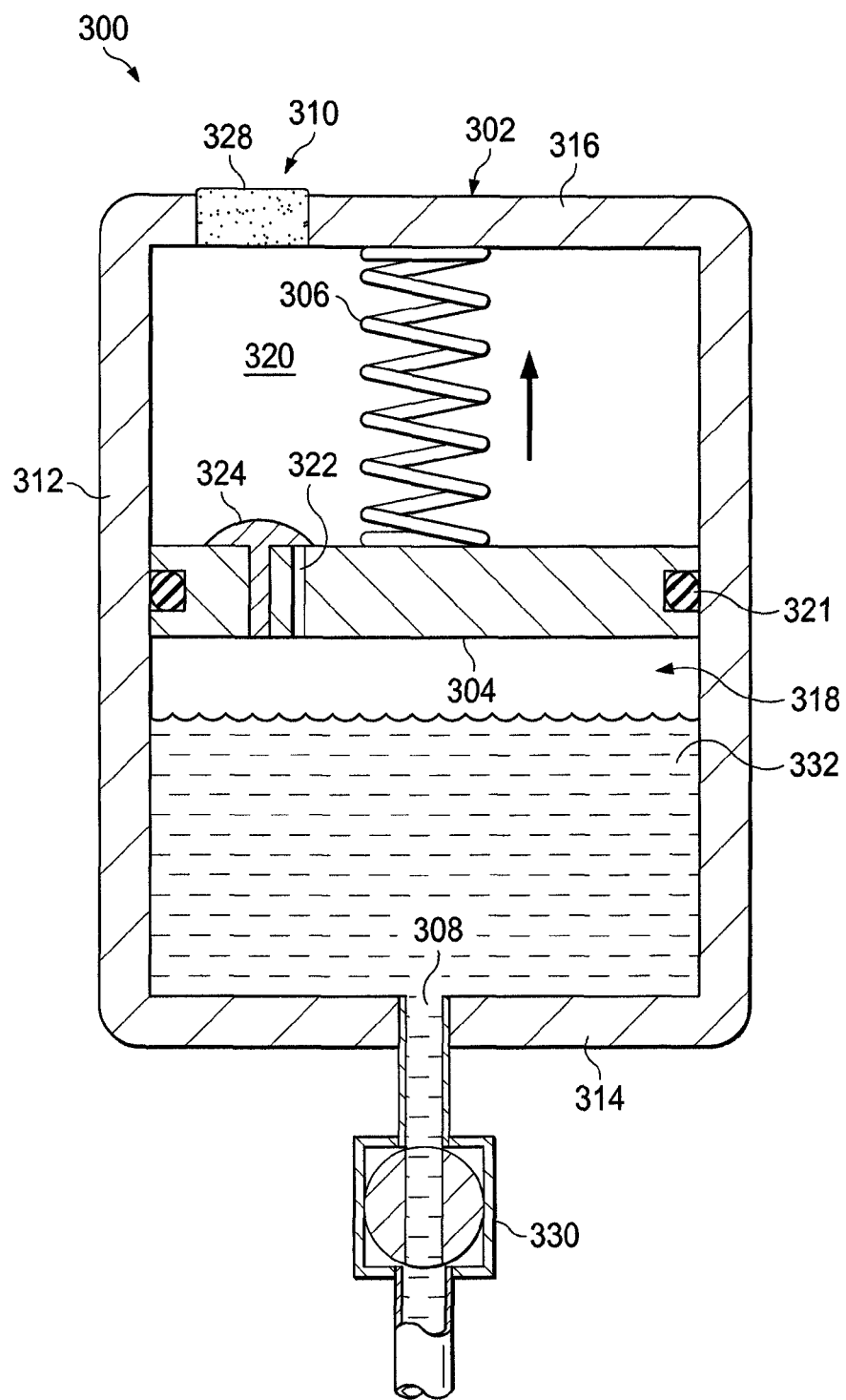
FIGS. 3A-3B are schematic diagrams illustrating additional details that may be associated with another example embodiment of a negative-pressure source in the negative-pressure therapy system of FIG. 1.
Figure 3B:
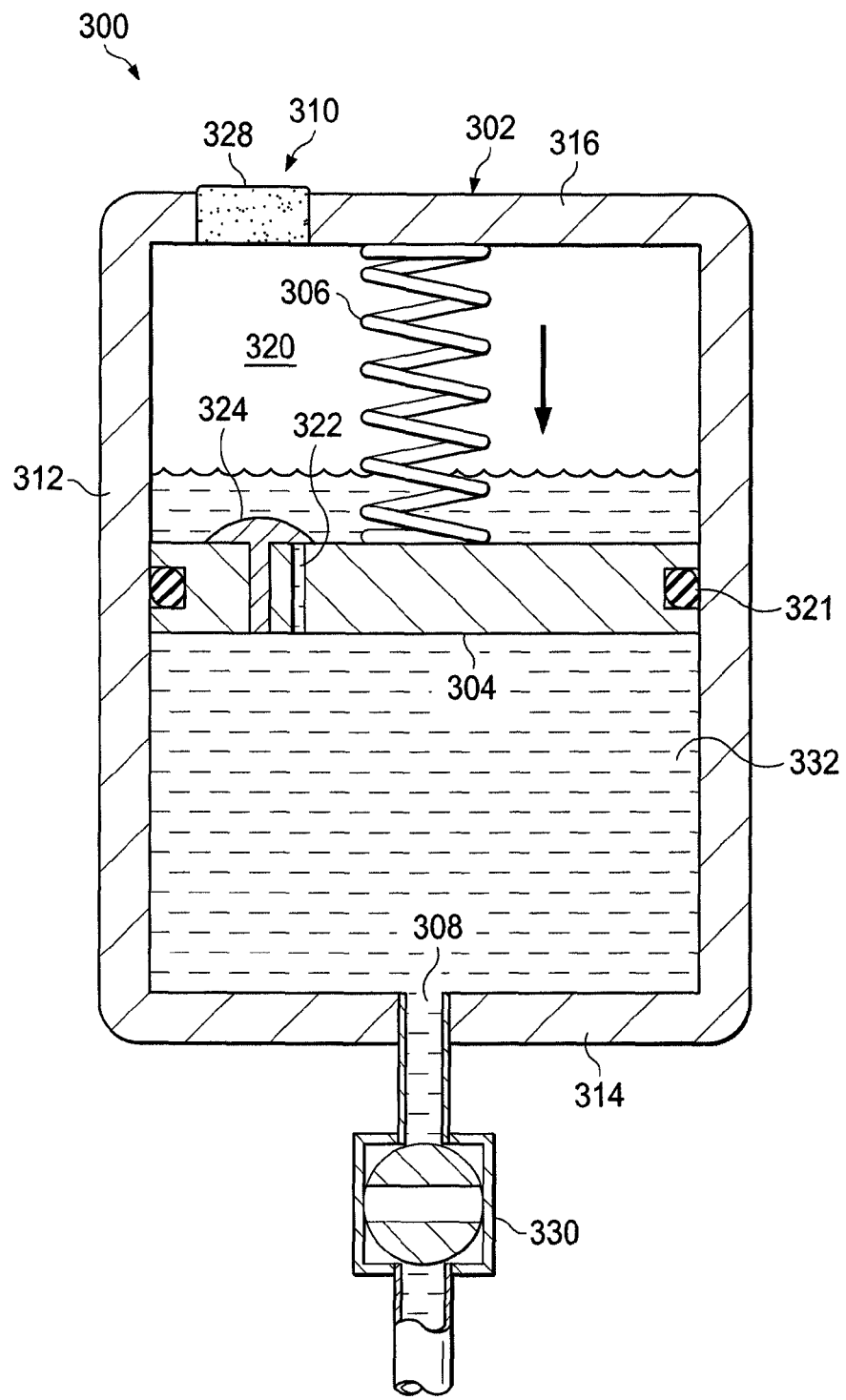

FIGS. 3A-3B are schematic diagrams of a pump 300 in two operational states, illustrating additional details that may be associated with other example embodiments of negative-pressure source 104. In this example embodiment, pump 300 may include a piston chamber 302, a piston 304, an elastic element 306, an intake port 308, and an exhaust port 310. Piston chamber 302 is similar in many respects to piston chamber 202. For example, piston chamber 302 is a substantially enclosed space, which may be generally defined by a cylinder having a side wall 312, a base 314, and a head 316, wherein base 314 and head 316 are generally coupled to opposing ends of side wall 312. Piston chamber 302 in this example embodiment is generally isolated from the ambient environment, except through intake port 308 and exhaust port 310.

Elastic element 306 is also analogous to elastic element 206 in most respects. Thus, elastic element 306 represents a spring or other means for storing mechanical energy. In some embodiments, for example, elastic element 306 may be a tension spring, a compression spring, a torsion spring, a constant spring, or a variable spring. Elastic element 306 may be operatively engaged to piston 304 to bias piston 304 away from intake port 308.

Piston 304 is generally disposed within piston chamber 302 and configured to move reciprocally within piston chamber 302. Piston 304 divides piston chamber 302 into a first chamber and a second chamber, such as vacuum chamber 318 and ambient pressure chamber 320. A seal 321 may also be disposed between piston 304 and side wall 312, such as in a groove on a side wall of piston 304, to prevent fluid flow between vacuum chamber 318 and ambient pressure chamber 320 along side wall 312. Intake port 308 may fluidly couple vacuum chamber 318 to a dressing, such as dressing 102. Exhaust port 310 can fluidly couple ambient pressure chamber 320 to the ambient environment.

As illustrated in FIGS. 3A-3B, piston 304 may be a substantially rigid barrier that can reciprocate within piston chamber 302. Piston 304 may be a cylinder or disk disposed within piston chamber 302, for example. Other embodiments may include alternative types of barriers, such as a flexible barrier that flexes within piston chamber 302, for example.

In the example embodiment of FIGS. 3A-3B, piston 304 is substantially solid with the exception of a conduit, passage, or port, such as passage 322, which fluidly couples vacuum chamber 318 and ambient pressure chamber 320. Thus, ambient pressure chamber 320 may be fluidly isolated from vacuum chamber 318 except through passage 322 in this illustrative embodiment. A valve 324 may be operatively coupled to piston 304 to control fluid flow between vacuum chamber 318 and ambient pressure chamber 320 through passage 322. For example, valve 324 may be a check valve or other unidirectional valve coupled to piston 304 or passage 322 that allows fluid to flow from vacuum chamber 318 to ambient pressure chamber 320, but blocks flow from ambient pressure chamber 320 to vacuum chamber 318. In other illustrative embodiments, passage 322 may be a gap between piston 304 and side wall 312, and valve 324 may be a flexible seal disposed around piston 304 configured to allow fluid to flow from vacuum chamber 318 to ambient pressure chamber 320 through the gap.

At least one liquid barrier may be disposed between ambient pressure chamber 320 and an ambient environment. For example, as illustrated in FIGS. 3A-3B, the liquid barrier may be a filter 328 disposed within, proximate to, or otherwise fluidly coupled to exhaust port 310 between ambient pressure chamber 320 and the ambient environment. Exhaust port 310 is preferably configured to allow gas to be expelled from ambient pressure chamber 320 as piston 304 moves toward exhaust port 310 during an operating stroke, and filter 328 may be configured to filter exudates and other liquids.

Filter 328 is analogous or similar to filter 228 in most respects. For example, filter 328 is preferably a gas-permeable, liquid-blocking filter. In yet more particular embodiments, filter 328 may be a sintered polymer filter that swells on contact with water. Suitable polymers include, for example, fluoropolymers such as PTFE, PVdF, or FEP; chlorofluoropolymers, such as PCTFE; polyolefins such as HDPE, PP, COC, or PMP; PVAc or EVA; PC; polyesters such as PET or PETG; or polysulphones or polyethersulphones. The polymer may also contain charcoal to reduce odor. Additionally, filter 328 may be coated to enhance hydrophobicity in some embodiments. Polymers may be formed into membranes or sintered (particularly for PVAc, EVA, polyolefin's, and fluoropolymers).

In more particular embodiments, a valve 330 may be coupled to intake port 308 to control fluid flow through intake port 308. For example, valve 330 may be a check valve or other unidirectional valve that allows fluid to flow through intake port 308 into vacuum chamber 318, but can block fluid in vacuum chamber 318 from being expelled through intake port 308, particularly during a charging stroke.

In operation, pump 300 may be charged by applying a charging force to move piston 304 toward intake port 308, which extends elastic element 306. For example, an operator may supply a charging force by applying hand pressure to a handle (not shown) coupled to piston 304, or by cranking a lever-based ratchet mechanism (not shown). The charging stroke decreases the volume of vacuum chamber 318. Since valve 330 may be configured to block fluid from flowing out through intake port 308 during a charging stroke, the decrease in volume of vacuum chamber 318 also increases the pressure in vacuum chamber 318. The increased pressure in vacuum chamber 318 may open valve 324 to allow fluid to flow from vacuum chamber 318 to ambient pressure chamber 320 during the charging stroke.

FIG. 3A illustrates a state of pump 300 during an operating stroke, in which piston 304 is moving away from intake port 308 within piston chamber 302. As FIG. 3A illustrates, an operating stroke may draw exudate 332 into vacuum chamber 318. Air from leaks, as well as other fluids, may also be drawn into vacuum chamber 318 during an operating stroke. However, valve 324 is generally closed during an operating stroke, blocking the flow of exudates 332 and other fluids into ambient pressure chamber 320.

If air from the ambient environment leaks into vacuum chamber 318, the pressure in vacuum chamber 318 generally increases. Similar to piston 204 in pump 200, a differential force and an elastic force act on piston 304. A pressure increase in vacuum chamber 318 causes the differential force to decrease, and elastic element 306 may move piston 304 away from intake port 308 to increase the volume of vacuum chamber 318. The increased volume of vacuum chamber 318 reduces the pressure in vacuum chamber 318 until reaching an equilibrium between the differential force and the elastic force. Thus, a therapeutic pressure may be maintained at a substantially stable level until piston 304 reaches a limit of the operating stroke.

Pump 300 may be recharged at any time during an operating stroke to maintain or extend therapeutic pressure. For example, pump 300 may be recharged at the end of an operating stroke to maintain therapeutic pressure. Pump 300 may be recharged by applying a charging force to piston 304 again, which moves piston 304 toward intake port 308 and extends elastic element 306 again, as illustrated in FIG. 3B. Valve 330 can be configured to prevent fluids in vacuum chamber 318 from being expelled through intake port 308 during a charging stroke. Valve 324 can be configured to allow exudate, air, and other fluids to be expelled through passage 322, transferring fluids from vacuum chamber 318 to ambient pressure chamber 320 during a charging stroke, also illustrated in FIG. 3B. Valve 324 may also be configured to block fluids in ambient pressure chamber 320 from being expelled through passage 322 into vacuum chamber 320 during an operating stroke (see FIG. 3A). Thus, during an operating stroke, piston 304 presses fluids in ambient pressure chamber 320 toward exhaust port 310. As piston 304 moves toward exhaust port 310, air and other gases may be expelled through exhaust port 310, but filter 328 retains exudate and other liquids in ambient pressure chamber 320. Consequently, gases are effectively separated from liquids and piston 304 may continue to move toward exhaust port 310 until all or substantially all gases have been expelled from ambient pressure chamber 320 into the ambient environment, or until otherwise reaching a limit of an operating stroke.

Figure 4:
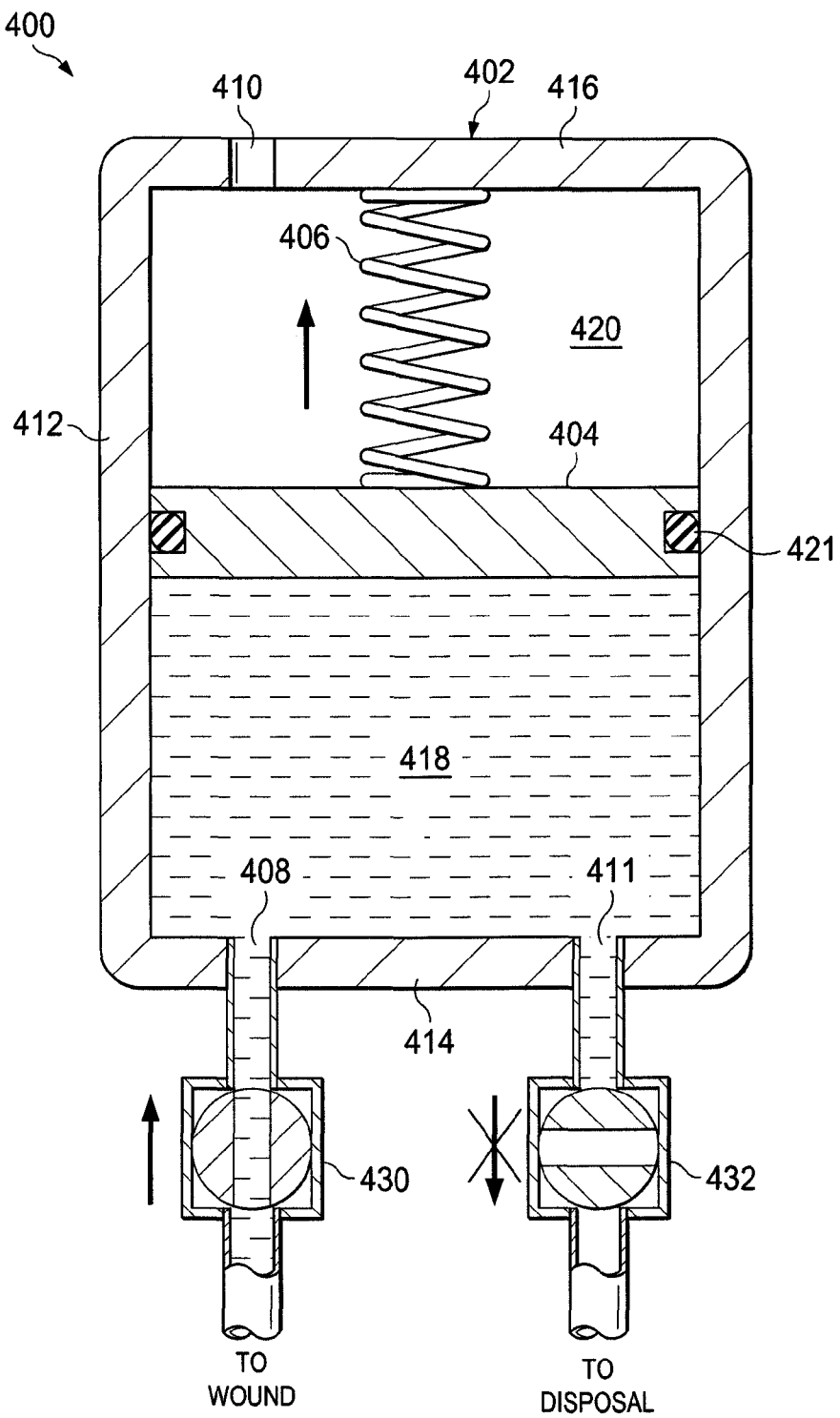
FIG. 4 is a schematic diagram illustrating additional details that may be associated with yet another example embodiment of a negative-pressure source in the negative pressure therapy system of FIG. 1.

FIG. 4 is a schematic diagram of a pump 400 illustrating additional details that may be associated with yet another example embodiment of negative pressure source 104. In this example embodiment, pump 400 may include a piston chamber 402, a piston 404, an elastic element 406, an intake port 408, an exhaust port 410, and a disposal port 411. Piston chamber 402 is similar in many respects to piston chamber 202 and piston chamber 302. For example, piston chamber 402 may be a substantially enclosed space generally defined by a cylinder having a side wall 412, a base 414, and a head 416, wherein base 414 and head 416 are generally coupled to opposing ends of side wall 412. Piston chamber 402 in this example embodiment is generally isolated from the ambient environment, except through intake port 408, exhaust port 410, and disposal port 411. As illustrated in FIG. 4, intake port 408 and disposal port 411 are preferably disposed within or fluidly coupled to base 414, and exhaust port 410 is preferably disposed within or fluidly coupled to head 416.

Elastic element 406 is also analogous to elastic element 206 and elastic element 306 in most respects. Thus, elastic element 406 represents a spring or other means for storing mechanical energy. In some embodiments, for example, elastic element 406 may be a tension spring, a compression spring, a torsion spring, a constant spring, or a variable spring. Elastic element 406 may be operatively engaged to piston 404 to bias piston 404 away from intake port 408.

Piston 404 is generally disposed within piston chamber 402 and configured to move reciprocally within piston chamber 402. Piston 404 divides piston chamber 402 into two chambers, such as vacuum chamber 418 and ambient pressure chamber 420. A seal 421 may also be disposed between piston 404 and side wall 412, such as in a groove on a side wall of piston 404, to prevent fluid flow between vacuum chamber 418 and ambient pressure chamber 420 along side wall 412. Intake port 408 may fluidly couple vacuum chamber 418 to a dressing, such as dressing 102. Exhaust port 410 can fluidly couple ambient pressure chamber 420 to the ambient environment. Disposal port 411 can fluidly couple vacuum chamber 418 to an external container, such as a remote canister or bag, or to a plumbed drain, for example.

Piston 404 may be a substantially rigid barrier that can reciprocate within piston chamber 402. Piston 404 may be a cylinder or disk disposed within piston chamber 402, for example. Other embodiments may include alternative types of barriers, such as a flexible barrier that flexes within piston chamber 402, for example.

In the example embodiment of FIG. 4, piston 404 is substantially solid. Thus, ambient pressure chamber 420 may be fluidly isolated from vacuum chamber 418 in this illustrative embodiment.

In more particular embodiments, a valve 430 may be coupled to intake port 408 to control fluid flow through intake port 408, and a valve 432 may be coupled to disposal port 411 to control fluid flow through disposal port 411. For example, either valve 430 or valve 432, or both, may be a check valve or other unidirectional valve. Valve 430 may be configured to allow fluid to flow through intake port 408 into vacuum chamber 418, but to block fluid in vacuum chamber 418 from being expelled through intake port 408, particularly during a charging stroke. Valve 432 may be a unidirectional valve configured to allow fluid to flow through disposal port 411 from vacuum chamber 418, but to block fluid from flowing into vacuum chamber 418 through disposal port 411.

In operation, pump 400 may be charged similarly to pump 200 or pump 300. For example, pump 400 may be charged by applying a charging force to move piston 404 toward intake port 408, which extends elastic element 406. The charging stroke decreases the volume of vacuum chamber 418. Since valve 430 may be configured to block fluid from being expelled through intake port 408 during a charging stroke, any fluid contained within vacuum chamber 418 during a charging stroke can be expelled through disposal port 411 and valve 432.

If air from the ambient environment leaks into vacuum chamber 418, the pressure in vacuum chamber 418 generally increases. Similar to piston 204 and piston 304, a differential force and an elastic force act on piston 404. A pressure increase in vacuum chamber 418 causes the differential force to decrease, and the resulting change in the net force may move piston 404 away from intake port 408 to increase the volume of vacuum chamber 418. The increased volume of vacuum chamber 418 reduces the pressure in vacuum chamber 418 until reaching an equilibrium between the differential force and the elastic force. Thus, a therapeutic pressure may be maintained at a substantially stable level until piston 404 reaches a limit of the operating stroke.

Pump 400 may also be recharged at any time during an operating stroke to maintain or extend therapeutic pressure. For example, pump 400 may be recharged at the end of an operating stroke to maintain therapeutic pressure. Pump 400 may be recharged by applying a charging force to piston 404 again, which moves piston 404 toward intake port 408 and extends elastic element 406 again. Valve 430 can be configured to prevent fluids in vacuum chamber 418 from being expelled through intake port 408 during a charging stroke. Valve 432 can be configured to allow exudates, air, and other fluids to be expelled through disposal port 411 during a charging stroke. Thus, during a charging stroke, piston 404 expels fluids in vacuum chamber 418 through disposal port 411, which can be fluidly coupled directly to an external container or through a plumbed drain, for example. The external container preferably has capacity to store fluids from more than one charging stroke.

The systems and methods described herein may provide significant advantages, some of which have already been mentioned. For example, negative-pressure therapy system 100 can manage wound fluids to enable recharging a manually-actuated negative-pressure source. In some embodiments, exudate may be separated from air, and fluid storage may be integrated with the negative-pressure source to reduce the number of components. In other embodiments, exudates and other fluids may be expelled to an external container. Negative-pressure therapy system 100 may be recharged without disconnecting the negative-pressure source, and is also generally tolerant to leaks during therapy. Negative-pressure therapy system 100 may be particularly advantageous for providing therapy without external fluid storage, but some embodiments of negative-pressure therapy system 100 may also be combined with or include external fluid storage, such as dressing with an absorbent layer or an external canister.

It should be apparent from the foregoing that novel and useful apparatuses, systems, and methods having significant advantages have been described. While shown in only a few forms, the apparatuses, systems, and methods illustrated are not mutually exclusive. Thus, features of one embodiment may be combined with features of other embodiments. Moreover, the illustrative embodiments are susceptible to various changes and modifications without departing from scope of the appended claim.

We claim:

1. A system for applying negative-pressure therapy, the system comprising:
    a dressing;
    a pump for applying negative pressure to the dressing, the pump comprising a vacuum chamber, an ambient pressure chamber, a port configured to couple the ambient pressure chamber to an ambient environment, a valve between the vacuum chamber and the ambient pressure chamber and configured for unidirectional flow from the vacuum chamber through a passage to the ambient pressure chamber during a charging stroke, a liquid filter configured to retain liquid in the pump, a piston disposed between the vacuum chamber and the ambient pressure chamber, and an elastic element operatively engaged to the piston, wherein the charging stroke comprises movement of the piston to store energy in the elastic element; and
    a lumen fluidly connecting the dressing to the vacuum chamber.

2. The system of claim 1, further comprising a second valve operatively coupled to the lumen and configured to block fluid flow from the vacuum chamber through the lumen during the charging stroke.

3. The system of claim 1, wherein the liquid filter is configured to retain liquid in the vacuum chamber during the charging stroke.

4. The system of claim 1, further comprising a container disposed within the vacuum chamber; and wherein the liquid filter is disposed between an interior of the container and the valve.

5. The system of claim 1, wherein the liquid filter is configured to retain liquid in the ambient pressure chamber during an operating stroke.

6. The system of claim 1, wherein the passage is disposed through the piston.

7. The system of claim 1, wherein the elastic element comprises a spring.

8. The system of claim 1, wherein the elastic element compresses to store the energy during the charging stroke.

9. The system of claim 1, wherein the elastic element expands to store the energy during the charging stroke.

10. The system of claim 1, wherein the liquid filter is configured to separate gas from liquid during the charging stroke.

11. The system of claim 1, further comprising a pouch positioned in the vacuum chamber, wherein the pouch is configured to retain liquids and gases, and wherein the pouch is configured to expel the retained gas while retaining the liquids when the pouch is compressed.

12. The system of claim 1, further comprising a second valve configured to provide unidirectional flow from the lumen to the vacuum chamber when the pump applies negative pressure to the dressing.

* * * * *